United States Patent [19]

Shen

[11] Patent Number: 5,360,878
[45] Date of Patent: Nov. 1, 1994

[54] HIGHLY CROSSLINKED SILICON POLYMERS FOR GAS CHROMATOGRAPHY COLUMNS

[75] Inventor: Thomas C. Shen, San Jose, Calif.

[73] Assignee: The United States of America as represented by the Administrator of the National Aeronautics and Space Administration, Washington, D.C.

[21] Appl. No.: 106,183

[22] Filed: Jul. 26, 1993

Related U.S. Application Data

[63] Continuation-in-part of Ser. No. 851,380, Mar. 4, 1992, abandoned.

[51] Int. Cl.$^5$ .......... C08G 77/20; C08F 2/48
[52] U.S. Cl. .......... 525/477; 528/10; 528/14; 528/32; 528/24; 522/99
[58] Field of Search .......... 528/10, 14, 32; 525/477; 522/99; 55/386

[56] References Cited

U.S. PATENT DOCUMENTS

| | | | |
|---|---|---|---|
| 3,624,030 | 11/1971 | Pruvost et al. | 528/12 |
| 3,639,498 | 2/1972 | Vlismas | 528/32 |
| 3,666,530 | 5/1972 | Aue | 117/54 |
| 3,878,092 | 4/1975 | Fuller | 210/31 |
| 4,045,353 | 8/1977 | Kosaka | 210/502 |
| 4,145,506 | 3/1979 | Yamamoto et al. | 528/10 |
| 4,324,689 | 2/1980 | Shah | 252/428 |
| 4,446,105 | 5/1984 | Dinsmoore | 422/70 |
| 4,626,556 | 12/1986 | Nozue et al. | 522/99 |
| 4,732,887 | 3/1988 | Obanaya | 502/402 |
| 4,826,943 | 5/1989 | Ito et al. | 528/21 |

Primary Examiner—John C. Bleutge
Assistant Examiner—Margaret W. Glass
Attorney, Agent, or Firm—Guy Miller; Darrell G. Brekke; John R. Manning

[57] ABSTRACT

A new highly crosslinked silicone polymer particle for gas chromatography application and a process for synthesizing such copolymer. The new copolymer comprises vinyltriethoxysilane and octadecyltrichlorosilane. The copolymer has a high degree of crosslinking and a cool balance of polar to nonpolar sites in the porous silicon polymer assuring fast separation of compounds of variable polarity.

18 Claims, 2 Drawing Sheets

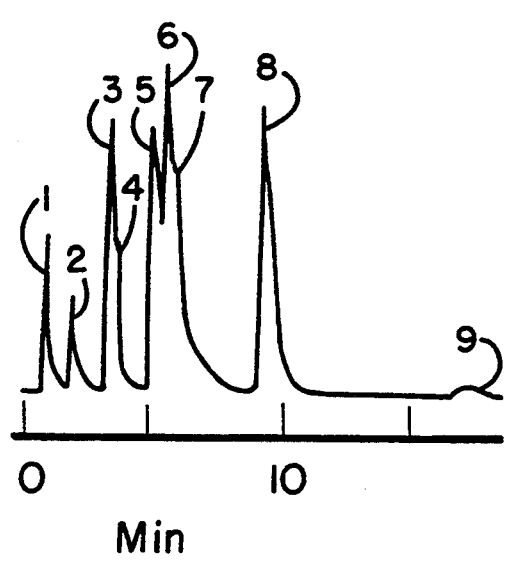
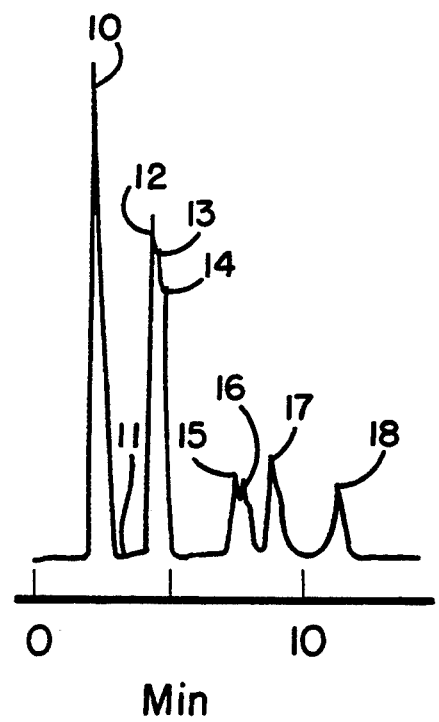
FIGURE 1
FIGURE 2

HIGHLY CROSSLINKED SILICON POLYMERS FOR GAS CHROMATOGRAPHY COLUMNS

The invention disclosed herein was made in the performance of work under NASA contract and is subject to public Law 96-517 (35 U.S.C. §200 et sec.). The contractor has not elected to retain title in this invention.

This application is a continuation-in-part of application Ser. No. 07/851,380, filed Mar. 4, 1992, now abandoned.

BACKGROUND OF THE INVENTION

1. Field of the Invention

This invention concerns a new highly crosslinked silicone polymer particle for gas chromatography application and a process and method for synthesizing such polymer. The new copolymer comprises vinyltriethoxysilane and octadecyltrichlorosilane. In particular, this invention concerns a polymer having a high degree of crosslinking and a good balance of polar to nonpolar sites in the porous silicon polymer resulting in a good separation of compounds of variable polarity. The new polymer also prevents bleeding or tailing of the stationary phase.

2. Related Disclosures

Gas and liquid chromatography columns for separation and analyses of the solutes of liquid samples have long been known and used in research and industry. Gas chromatography has also been successfully employed in the space projects. Both the Viking and Pioneer Venus missions had gas chromatograph on board and used it for analyses of various samples of atmosphere and surface materials. Gas chromatography has also been proposed for use in certain future missions, such as Comet Rendezvous Asteroid Flyby and Cassini Saturn Mission which require the precise determination of polar and nonpolar chemicals in minuscule amounts.

For these missions, a highly sensitive detector spectrometer combination consisting of metastable ionization detector and ion mobility spectrometer was developed. This detector, however, is extremely sensitive to column bleed associated with the conventional liquid phases coated on solid supports. Chromatograms using these detectors with column containing liquid phases on solid support are usually very noisy, having a rough base line. While silicone liquid phases on solid supports are known to provide good separations of polar as well as non-polar compounds, the bleeding problem usually persists.

It would thus be very useful to have available a material which would avoid the bleeding problems but still provide a good separation of polar and non-polar compounds.

Many chromatographic support materials have been developed with time. U.S. Pat. No. 4,767,529 describes nitro group-containing modified chromatographic support material and discusses in general the use of a globular, hydrophilic vinyl polymer modified with m-aminophenylboric acid after epoxidation. These vinyl polymers have a high mechanical and chemical stability and good compatibility with organic solvents.

U.S. Pat. No. 4,446,105 describes the use of octadecylsilane and cyano propylsilane as absorbents in chromatographic columns particularly suitable to identify hydrocarbon components of fuels produced by liquefaction of coal.

U.S. Pat. No. 4,045,353 discloses a solid chromatography support which has a high separation ability, accommodates a high load of the sample and does not cause the elution of a polymer. The solid support is prepared by the absorption of polymerizable monomer onto a micro-porous inorganic substrate. The suitable monomers include ethylenically unsaturated monomers such as styrene monomers, fluorine monomers, such as tetrafluoroethylene, silicon containing monomers such as vinyltriethoxysilane, acrylates or other vinyl monomers.

U.S. Pat. No. 3,878,092 relates to chromatographic analyzers utilizing a chromatographic column which column is provided with a partitioning agent comprising a crosslinked polymeric material bonded to an interior of the column either directly or through an intermediate film or coupling agent. The coupling agent, which may be vinyltriethoxysilane, is used to coat the interior wall surface of the chromatographic column and must have reactive groups capable of chemically reacting with the column wall.

Vinyltriethoxysilane used as silylating agent is described in U.S. Pat. No. 4,732,887. A process for preparation of octadecyltrichlorosilane is disclosed in U.S Pat. No. 3,666,530 and its use in preparation of a reverse-phase chromatographic packing is disclosed in U.S. Pat. No. 4,324,689.

While some of these patents contain some improvements with respect to their intended utilities, none does achieve a polymer having properties most desirable for space use, demanding the highest degree of accuracy in shortest possible time.

It is, therefore, a primary object of this invention to prepare a gas chromatography column packing (stationary phase) which would avoid the bleeding problems but have a good separation of a wide variety of compounds of variable polarities. The new polymer having octadecyltrichlorosilane and vinyltriethoxysilane as starting comonomers produce uncrosslinked intermediate polymer, which is then crosslinked to produce the crosslinked, porous, polymer particle which is insoluble in most organic solvents, of the present invention having such qualities.

SUMMARY

One aspect of this invention is a new porous silicon polymer column packing of high stability and high separation properties.

Another aspect of this invention is a new porous silicon polymer which prevents a column bleeding and is able to separate polar compounds as well as non-polar compounds.

Still another aspect of this invention are porous silicon polymers able to separate polar compounds, such as amines having 1–4 carbons, alcohols having 1–4 carbons and hydrocarbons having 1–8 carbons.

Still yet another aspect of this invention are porous silicon polymers which are produced from comonomers of vinyltriethoxysilane and octadecyltrichlorosilane.

BRIEF DESCRIPTION OF DRAWINGS

FIG. 1 represents a gas chromatogram of various amines using a column produced by polymerizing vinyltriethoxysilane and octadecyltrichlorosilane as comonomers.

FIG. 2 represents a gas chromatogram of saturated and nonsaturated hydrocarbons using a vinyltriethoxy silane/octadecyltrichlorosilane column.

DETAILED DESCRIPTION OF THE INVENTION

Figure 3:
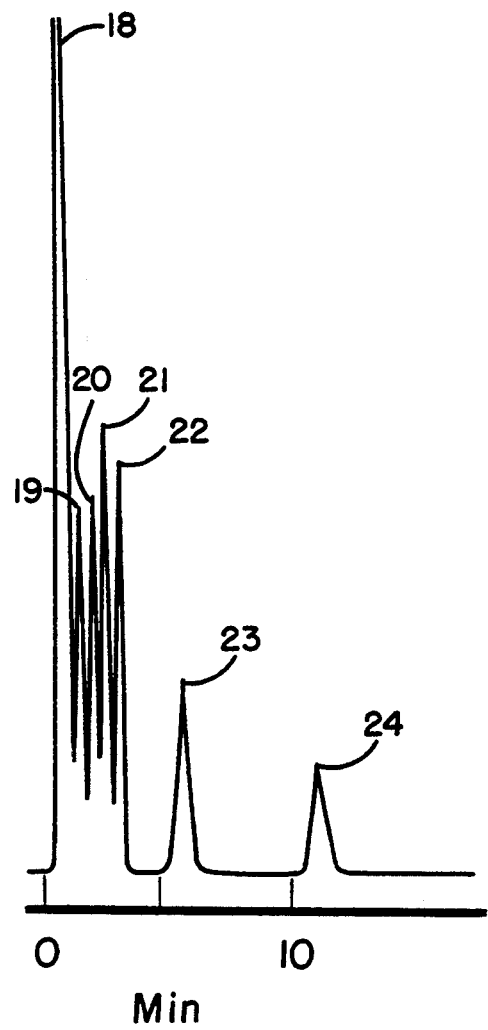
FIG. 3 represents a gas chromatogram of alcohols using a column produced from the polymerization of vinyltriethoxysilane and octadecyltrichlorosilane as comonomers.

This invention concerns a new porous silicone containing polymer useful as a stationery phase solid particle packing for gas chromatographic column. The unique composition of the new stationary phase has improved properties against previously described materials and detector-spectrometer combinations. The primary improvements achieved by this invention are the avoidance of bleeding of the stationary phase and an excellent and fast separation of a wide variety of compounds of variable polarities.

The new solid porous silicone polymers of the current invention consist of two groups which are obtained from two general chemical groups, unsaturated organic silane and alkyl trihalosilane, namely vinyl siloxyl groups and higher alkyl halosilane groups, preferably vinyltriethoxysilane and octadecyltrichlorosilane. The polymer having a molar ratio of 1–4:0.1–2, preferably 2:1, of vinyltriethoxysilane to octadecyltrichlorosilane gives a high degree of crosslinking and a remarkable balance of polar/nonpolar sites in the porous solid polymer. This balance of polar and nonpolar sites is responsible for excellent separation of polar and non-polar compounds. The high degree of crosslinking of the polymer which is not soluble in most organic solvents is responsible for lack of bleeding of the stationary phase made of such copolymer. The high degree of crosslinking of the copolymer is at least about 30% or greater, preferably is about 50% or greater, more preferably is about 60% or greater, and especially preferred is about 65% or greater.

These new properties are results of the current discovery which utilizes trichlorosilane and vinyl groups and applies a free radical polymerization process to obtain this new high crosslinked solid porous octadecyl trichlorosilane and vinyltriethoxysilane polymer. The organic solvents the polymer particle is not soluble in includes, for example, acetone, ethanol, carbon tetrachloride, chloroform, methylene chloride, hexane, benzene, toluene, diomethylamine, methyl ethyl ketone, ethyl acetate and the like.

In general, trichlorosilane condensation polymerization induces low or non-crosslinking polymers in organic solvents. This reaction can be explained by the following equation:

$RSi(OR)_3 + H_2O \longrightarrow$

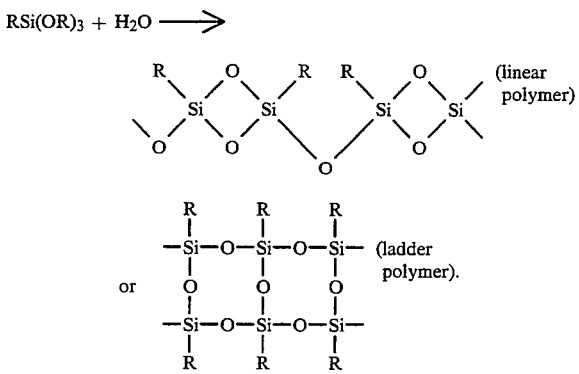

Both these linear and ladder trichlorosilane polymers are soluble in organic solvents, such as heptane, tetrahydrofuran, etc., and therefore, are not useful for GC column applications. That is particularly so because of their excessive absorption properties at low temperatures.

Since, however, literature (*Chromatographia*, 9:219 (1976) and 10:466 (1977)), indicates that silicone liquid stationary phases on solid supports provide good separation of polar as well as non-polar compounds, attempts were made to use this knowledge in synthesizing solid yet porous high crosslinked polymer which would prevent the bleeding and tailing of the stationary phase usually observed with other stationary phases. These attempts resulted in the current invention.

Vinyl resins have been used advantageously in various industries. These polymers provide many desirable qualities such as strength and adhesivity suitable for molding compositions, surface coating, manufacture of synthetic fibers, etc. In this invention, vinyl silicone derivatives, such as methacryloxypropyl triethoxysilane or vinyltrichlorosilane, preferably vinyltriethoxysilane, are used to achieve high crosslinking and prevent bleeding.

Trichlorosilanes, such as hexadecyltrichlorosilane, dodecyltrichlorosilane, preferably octadecyltrichlorosilane, are used to achieve the good separation of materials having various polarity.

In one embodiment of the present invention, for example, the higher alkyl trichlorosilane, $R^1SiCl_3$, is combined with the vinyl-type trialkoxy silane as shown below:

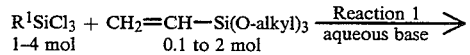

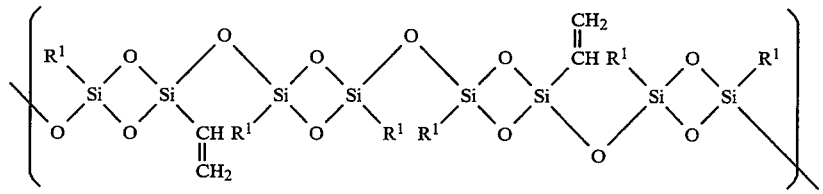

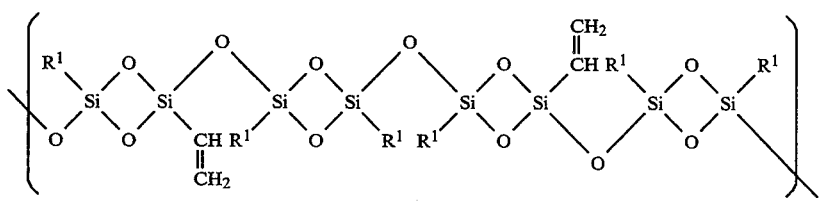

LINEAR NONCROSSLINKED POLYMER CHAINS
(plus other noncrosslinked ring structures)

The polysiloxanes as linear noncrosslinked polymer chains containing the pendant C=C groups are then crosslinked through the pendant C=C group using a chemical initiator or photoinitiation to produce the crosslinked insoluble in most organic solvents, porous polymer particles of the present invention as shown below:

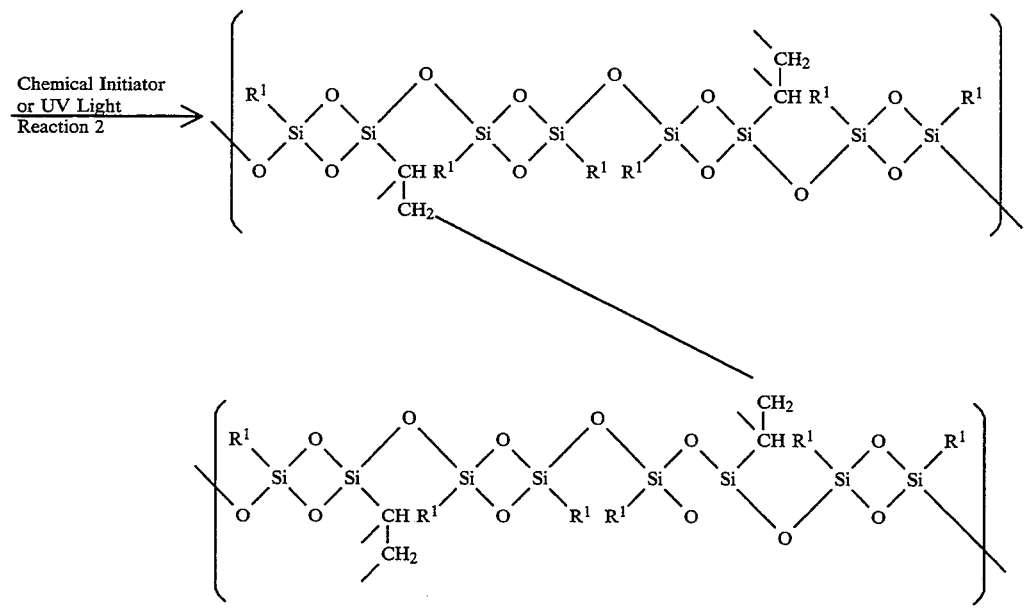

In order to make highly crosslinked polymers, vinyl groups were added to trichlorosilanes and a free radical polymerization was applied. The condensation polymerization and followed by a free radical polymerization of vinyl and trichlorosilane components, particularly vinyltriethoxysilane with octadecyltrichlorosilane, was found to form highly crosslinked polymers not soluble in most organic solvents. Several polymerizations with various mole ratios ranging from 1–4 moles of vinyltriethoxysilane to 0.1–2 moles of octadecyltrichlorosilane were carried out. For most polymers, the vinylsiloxyl comonomer is present as SiO, $SiO_{3/2}$ and $SiO_4$. Preferably, the vinylsiloxyl groups are present as $SiO_{3/2}$. While these polymers provided reasonably good separation and/or prevented bleeding, the best results were obtained when the polymer product had a 2:1 mole ratio. The vinyltriethoxysilane/octadecyltrichlorosilane (2:1) polymer provided the best balance of polar and non-polar groups as well as good separation and peak symmetry for many polar and nonpolar compounds. The polymer is also almost completely void of bleeding.

The polymers according to this invention are prepared by adding 3.5–14 grams (0.018–0.074 mole) preferably 7.0 grams (0.037 mole) of vinylsilane, preferably vinyltriethoxysilane, obtained from Petrarch Systems, (Bristol, Pa.) to 0.7–14 (0.018–0.037 mole), preferably 7 grams (0.018 mole) of trichlorosilane, preferably octadecyltrichlorosilane, obtained from Aldrich Chemical Company, Milwaukee, Wis. The combined mixture is added to 50 ∝ 200 ml of aqueous basic solution, preferably to 70 ml of 0.1% of sodium hydroxide, under constant stirring, at temperature from 15°–40° C., preferably at room temperature. After stirring for 10–60 minutes, preferably after 20 minutes, the solid polymer forms. Dilute base also includes aqueous sodium hydroxide, potassium hydroxide, calcium hydroxide and the like in a concentration of between about 0.5 and 0.001 percent by weight. Preferred base is sodium hydroxide in between about 0.4 and 0.01 percent by weight, more preferably about 0.1 percent by weight.

The solid polymer is filtered and washed several times with water alcohol mixture, preferably with methanol water (1:1) to remove any hydroxide residue. After drying under vacuum at temperature 25°–60° C., preferably at 45° C., the polymer is transferred to a reaction flask equipped with a condenser, thermometer, addition funnel and mechanical stirrer. The polymer is dissolved in an organic solvent, preferably in heptane with stirring, the flask is swept with nitrogen to remove air, and the temperature is raised to 65°–90° C., preferably to 80° C. The polymerization is started with adding of polymerization initiator or by UV initiation, preferably with azobisisobutyronitrile, dissolved in aliphatic ketone such as acetone, pentanone, cyclohexanone, and such others, preferably in 10 ml of methylethylketone.

The initiator is added in a short period of time between 1-5 minutes, preferably within 2 minutes.

The polymerization and crosslinking is continued for 2-6 hours, preferably for 3 hours. The mixture is then cooled to a temperature from 15°-40° C. preferably to a room temperature. The formed particles are suction filtered and washed with aliphatic cyclic ether, such as furan, dioxane, tetrahydropyran, preferably with tetrahydrofuran, and with hydrocarbon such as hexane or, preferably, petroleum ether, at temperature from 30°-70° C., preferably at 40°-60° C. The particles are dried in vacuum at temperature around 100° C., for 4-10 hours, preferably for 6 hours. The detailed procedure is described in Example 1.

The gas chromatographic evaluation of synthesized particles is performed after particles are sieved and the 80-100 mesh fraction is separated. Using generally known procedures, the gas chromatographic column was packed and detector and helium carrier gas were utilized to demonstrate the separation of various compound classes and polarities.

FIGS. 1-5 illustrate obtained results. Compounds such as saturated and unsaturated hydrocarbons, pentane, 3,3-dimethyl-1-butene, hexane, 2, 2, 4-trimethyl pentane, heptane, 2, 4, 4-trimethyl-2-pentane, and 2, 3, 4-trimethyl pentane, (FIG. 2); unsaturated hydrocarbons, 1-hexene, 2-hexane, (FIG. 4); alcohols, such as methanol, ethanol, isopropanol, t-butanol, propanol, isobutyl alcohol, and butanol (FIG. 3), nitriles, such as acetonitrile, or acrylonitrile, (FIG. 5), and amines, trimethylamine, methylamine, t-butylamine, ammonia, diethylamine, diethylmethylamine, sec-butylamine, triethylamine, and pyridine (FIG. 1), were separated by the gas chromatography. Gas chromatograms of compounds named above were obtained using a vinyltriethoxysilane/octadecyltrichlorosilane column (6 ft × 1/16 inch stainless steel) at temperature 107° C. and with flow of 13 ml/minute of helium as the carrier gas.

Figure 4:
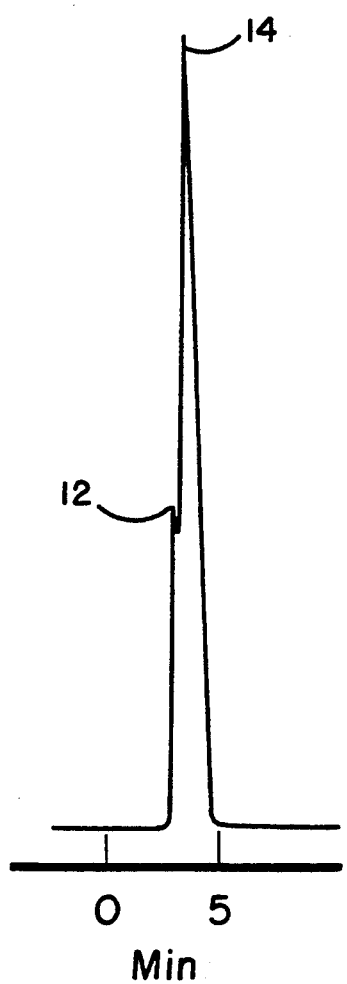
FIG. 4 represents a gas chromatogram of unsaturated hydrocarbons using vinyltriethoxysilane and octadecyltrichlorosilane as comonomers.
Figure 5:
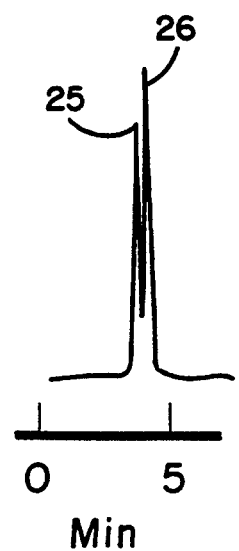
FIG. 5 represents a gas chromatogram of nitriles using a column produced from the polymerization of vinyltriethoxysilane and octadecyltrichlorosilane as comonomers.

The results of chromatographic separation using a new polymer column, as a function of time, are shown in FIGS. 1-5. FIG. 1 is the gas chromatogram of amines showing a good separation of such similar compounds as trimethylamine (1); methylamine (2); t-butylamine (3); ammonia (4); diethylamine (5); diethylmethylamine (6); secondary butylamine (7); triethylamine (8); and pyridine (9) in about 15 minutes. FIG. 2 is the gas chromatogram of the mixture of saturated and nonsaturated hydrocarbons containing pentane (1); 3,3-dimethyl-1-butene (2); 1-hexene (3); hexane (4); 2-hexene (5); 2, 2, 4-trimethylpentane (6); heptane (7); 2, 2, 4-trimethyl-2-pentene (8); and 2, 3, 4-trimethylpentane (9). In this case, with exception of hexane and hexene compounds 3, 4, and 5, all these compounds are also well separated into individual components in about 15 minutes. The separation of hexene and hexane is seen in FIG. 4. Among themselves, unsaturated hydrocarbons 1-hexene (1) and 2-hexene (2), seen in FIG. 4, were reasonably well separated already at 5 minutes. Alcohols as seen in FIG. 3, separated very well into methanol (1); ethanol (2); isoprophanol (3) t-butanol (4); and propanol (5); and into butyls isobutyl (6) and butanol (7). Nitriles, acetonitrile (1) and acrylonitrile (2), as seen in FIG. 5, separated early at 3-5 minutes to two distinct peaks.

These results illustrate an excellent separation properties of the new polymer without virtually any bleeding resulting from the new polymer containing columns. In a relatively very short time, between 1-19 minutes, all tested compounds separated clearly without observable tailing into their individual peaks.

UTILITY

New polymers of the current invention possess certain special properties making them particularly useful for space research. Future missions to Mars and other planets will require chemical analyses of their atmospheres and surface materials. For this purpose, silicone packed columns of high stability and separation properties have been developed. These columns can separate amines having 1-4 carbon, alcohols having 1-4 carbons and many hydrocarbons having 1-8 carbons with short retentions times needed for flight application.

The polymer produced by the polymerization of vinyltriethoxysilane and octadecytrichlorosilane with a molar ratio of 2:1 gave a high degree of crosslinking and a remarkable balance of polar/nonpolar sites in the porous, solid polymer. This polymer particle is particularly useful in GC for separating compounds of high variable polarity with very little or no tailing and short retention times suitable for future flight missions where the precise chemical analyses of the atmosphere and surface materials will be required almost instantly.

The utility of these polymers is not, however, limited to the use of space programs. Since they have such excellent separation properties of both polar and nonpolar compounds and since the separation is fast and clean because the material does not bleed during chromatography, these polymers will be equally useful for both gas and liquid chromatography routinely used in research and industry.

EXAMPLE 1

Preparation of New Octadecyltrichlorosilane and Vinyltriethoxysilane Copolymer

This example illustrates the preparation and testing of new polymers of this invention.

A. Preparation of Polymer

Into a stoppered 50 ml Erlenmeyer flash was weighed 7.0 grams (0.018 mole) of octadecyltrichlorosilane and 7.0 grams (0.037 mole) of vinyltriethoxysilane. This solution was added quickly to an aqueous, magnetically stirred solution of 0.1% of NaOH (70 ml) at room temperature. After stirring for 20 minutes, the solid polymer was filtered with suction through a Buchner funnel using Whatman #4 filter paper. The polymer was washed several times with aliquots of a (1:1) methanol-water mixture to remove any sodium hydroxide. After being vacuum dried at ca. 45° C. (yield 6.98 grams), the polymer was transferred to a round bottomed reaction flask with four standard taper fittings for a condenser, thermometer, addition funnel, and mechanical stirrer. The polymer was dissolved in 70 ml of heptane with stirring at 80 rpm. The flask was swept with nitrogen to remove air and the temperature of the solution was raised to 80° C. At this time, 0.32 grams of azobisisobutyronitrile (AIBN) initiator, dissolved in 10 ml of methylethyl ketone, was added within 2 minutes. Further polymerization and crosslinking was continued for 3 hours, after which the mixture was cooled to room temperature. The particles were suction filtered and washed with tetrahydrofuran and finally with petroleum ether at 40°-60° C. The particles were then dried in vacuum at 100° C. for six hours. The procedure yielded 6.85 grams of final polymer.

B. Gas Chromatographic Evaluation

For gas chromatographic evaluation, the polymer particles were sieved and the 80-100 mesh fraction was used to pack a 6 ft×1/16 inch stainless steel column. A Perkin-Elmer Sigma 3 gas chromatograph with a FID detector and helium carrier gas was utilized to demonstrate the separation of various compound classes and polarities, e.g., hydrocarbons, alcohols, and amines. Temperature was 107° C. and helium flow rates were 13 ml/minutes.

What is claimed is:

1. Porous, silicon-containing solid organic polymer particles which are formed from crosslinking intermediate polymer chains, wherein the degree of crosslinking is about 30% or greater, said intermediate polymer chains being formed from the polymerization of an alkyl trichlorosilane monomer unit, wherein the alkyl group is selected from dodecyl, hexadecyl or octadecyl, with substituted siloxyl group monomer units selected from $CH_2=CH-Si-(O-alkyl)_3$ or $CH_2=C(CH_3)-(C=O)-OCH_2CH_2CH_2Si-(O-alkyl)_3$.

2. The porous polymer particles of claim 1 wherein the molar ratio of the alkyl trichlorosilane monomer units to the substituted siloxyl group monomer units is between about 0.1-2:1-4.

3. The porous polymer particles of claim 1, wherein said alkyl of said alkyl trichlorosilane is octadecyl.

4. The porous polymer of claim 1, wherein said alkyl is hexadecyl.

5. The porous polymer of claim 1, wherein said alkyl is dodecyl.

6. The porous polymer particles of claim 3, wherein the substituted siloxyl group monomer is vinylsiloxyl.

7. The porous polymer particles of claim 6, wherein the molar ratio of vinylsiloxyl to octadecyltrichlorosilane is 2:1.

8. Improved porous, silicon-containing copolymer particles comprising intermediate polymer chains that are crosslinked and formed from comonomers:
(1) an alkyl trichlorosilane; and
(2) $CH_2=CHSi(O-alkyl)_3$ or $CH_2=C(CH_3)(C=O)OCH_2CH_2CH_2-Si(O-alkyl)_3$ wherein said alkyl trichlorosilane is selected from dodecyl, hexadecyl or octadecyl trichlorosilane and said (O—alkyl) is methoxy or ethoxy, said copolymer particles being crosslinked as a result of said intermediate polymer chains being crosslinked to one another, wherein said copolymer particles are obtained by a process comprising the steps of:
(a) mixing said alkyl trichlorosilane with methacryloxypropyltriethoxysilane or vinyltrialkoxysilane, where said alkyl trichlorosilane and said methacryloxypropyltriethoxysilane or vinyltrialkoxysilane are mixed in a molar ratio in the range of between about 0.1-2:1-4;
(b) polymerizing the mixture of step (a) by adding dilute aqueous base to form said intermediate polymer chains;
(c) separating the dilute aqueous base and the intermediate polymer chains;
(d) further polymerizing and crosslinking the polymer obtained in step (c) by first dissolving the polymer in an organic solvent and then either:
(1) adding a polymerization initiator, or
(2) irradiating with ultraviolet light;
(e) separating the crosslinked porous copolymer particles by filtration; and
(f) washing and drying the porous crosslinked copolymer particles, which are insoluble in most organic solvents.

9. The copolymer particles of claim 8, wherein the vinyltrialkoxysilane is vinyltriethoxysilane.

10. The copolymer particles of claim 8 wherein the vinyltrialkoxysilane is vinyltrimethoxysilane.

11. The copolymer particles of claim 9, wherein said alkyltrichlorosilane is octadecyltrichlorosilane.

12. The copolymer particles of claim 11, wherein the molar ratio of vinyltriethoxysilane to octadecyltrichlorosilane is 2:1.

13. The copolymer particles of claim 8, wherein the polymerization and crosslinking of step (d) is conducted in the presence of azobisisobutyronitrile as the initiator.

14. Improved, porous polymer particles for use as a stationary phase in a gas chromatographic column, wherein said polymer particles are crosslinked polymers insoluble in most organic solvents, which porous polymer particles consist essentially of:

silicon-containing polymer particles containing units of a dodecyl, hexadecyl or octadecyl siloxyl group and a substituted siloxyl group selected from

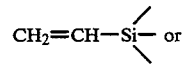

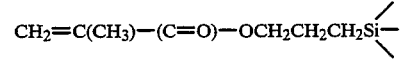

that are crosslinked by $CH_2=CH-$ linkages or by the $CH_2=C(CH_3)(C=O)-OCH_2CH_2CH_2-$ linkages.

15. The polymer particles of claim 14, wherein the molar ratio of said dodecyl, hexadecyl or octadecyl siloxyl group and said substituted

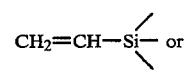

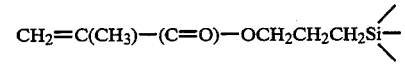

group is in the range between 0.1-2:1-4.

16. The polymer particles of claim 15, wherein units of octadecyl siloxyl are present.

17. The polymer particles of claim 15, wherein units of hexadecyl siloxyl are present.

18. The polymer particles of claim 16, wherein vinylsiloxyl and octadecylsiloxyl are present in a molar ratio of 2:1.

* * * * *